United States Patent [19]

Kronenthal et al.

[11] Patent Number: 5,245,055
[45] Date of Patent: Sep. 14, 1993

[54] PROCESS FOR PREPARING A CIS OXABICYCLO OLEFINIC ACID AND ESTER FROM AN OXABICYCLO PYRANOL

[75] Inventors: David Kronenthal, Yardley, Pa.; Robert Waltermire, Monmouth Junction, N.J.

[73] Assignee: E. R. Squibb & Sons, Inc., Princeton, N.J.

[21] Appl. No.: 629,507

[22] Filed: Dec. 18, 1990

[51] Int. Cl.$^5$ ............................................. C07D 307/00
[52] U.S. Cl. ................................................. 549/463
[58] Field of Search .......................................... 549/463

[56] References Cited

U.S. PATENT DOCUMENTS 4,413,054  3/1979  Sprague .............................. 260/346
4,663,336  5/1987  Nakane et al. ...................... 514/381

OTHER PUBLICATIONS

G. Guanti et al., Tetrahedron Letters, 27, 4639 (1986).
R. Bloch et al., Tetrahedron Letters, 26, 4087 (1985).
J. Bryan Jones et al., Can. J. Chem. vol. 62, 2578–2582 (1984).
K. P. Lok et al., J. Am. Chem. Soc. 107, 2521–2526 (1985).

Primary Examiner—C. Warren Ivy
Assistant Examiner—A. Owens
Attorney, Agent, or Firm—Timothy J. Gaul

[57] ABSTRACT

A compound having the structure

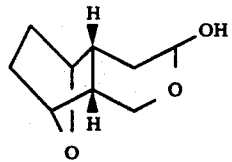

is reacted with $Ph_3P=CH(CH_2)_3Y$ wherein Y is $-CO_2^{\ominus}M^{\oplus}$ or $-C\equiv N$ to form

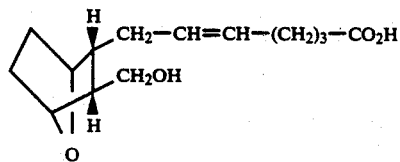

which is aminated and esterified to form

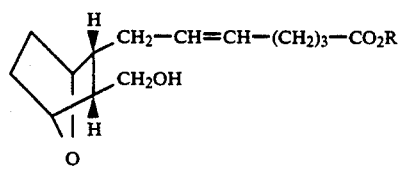

which may be used to form [1S-[1α,2α(Z),3α, 4α[[-7-[3-[[[(1-oxoheptyl) -amino]acetyl]amino]methyl]-7-oxabicyclo-[2.2.1]-hept-2-yl]-5-heptenoic acid.

18 Claims, No Drawings

PROCESS FOR PREPARING A CIS OXABICYCLO OLEFINIC ACID AND ESTER FROM AN OXABICYCLO PYRANOL

FIELD OF THE INVENTION

This invention relates to processes for preparing cis oxabicyclo olefinic acids from associated pyranols.

BACKGROUND OF THE INVENTION

[1S-[1α,2α(Z),3α,4α[[-7-3-[[[1-Oxoheptyl)-amino]acetyl]amino]methyl]-7-oxabicyclo-[2.2.1]hept-2-yl]-5-heptenoic acid is a cardiovascular agent useful, for example, in the treatment of thrombotic disease. U.S. Pat. No. 4,663,336, issued on May 5, 1987, describes a synthesis of this compound that begins with [1S-[1α,2α(Z), 3α,4α]]-7-[3-Hydroxymethyl-7-oxabicyclo-[2.2.1]-hept-2-yl]-5-heptenoic acid. Preparation of this latter compound is described in U.S. Pat. No. 4,143,054.

BRIEF DESCRIPTION OF THE INVENTION

In accordance with the present invention, a process is provided in which compound VII of Reaction Scheme 2 is prepared by reacting pyranol VI with ylide VI' in tetrahydrofuran, wherein Ph is phenyl and Y is —C≡N or $CO_2^{\ominus}M^{\oplus}$ and $M^{\oplus}$ is an alkali metal ion (potassium preferred).

Also in accordance with the present invention, a process is described in which compound VI' is prepared by reacting a phosphonium salt VI''

$Ph_3P^{\oplus}(CH_2)_4Y$ $Halo^{\ominus}$ wherein halo is preferred to be bromo and Y is —C≡N, $CO_2H$, or $CO_2^{\oplus}M^{\ominus}$ with an alkali metal butoxide, amylate, hydride or disilazide (e.g., potassium t-butoxide, potassium t-amylate, potassium hydride or potassium hexamethyldisilazide) in tetrahydrofuran, after which compounds VI and VI' react to form compound VII. Compound VI' may conveniently be prepared and used in situ in this process.

Further in accordance with the present invention, a process is provided wherein compound VII is neutralized to form amine salt VIII of Reaction Scheme 2 (wherein X is an amine, preferably adamantanamine) and then crystallized to remove any trans isomer impurity. The amine salt VIII may then be esterified to form compound IX in Reaction Scheme 2.

Further still in accordance with the present invention, compound IX as prepared above is used to prepare compound XIII of Reaction Scheme 3.

Reaction Scheme 1

Compounds A, B or C from Reaction Scheme 1 ——→

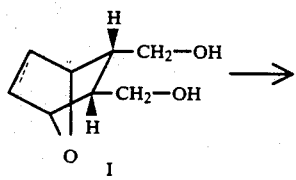

I

-continued
Reaction Scheme 1

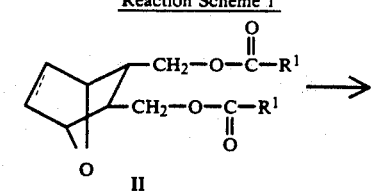

II

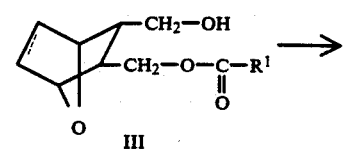

III

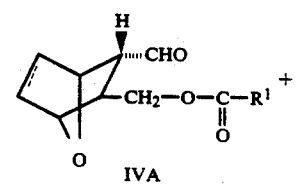

IVA +

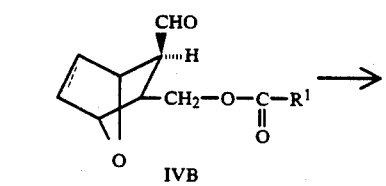

IVB

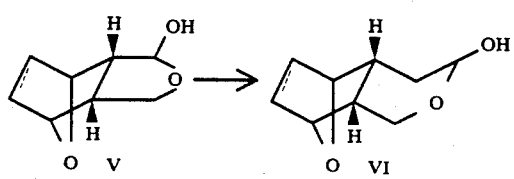

V    VI

Reaction Scheme 2

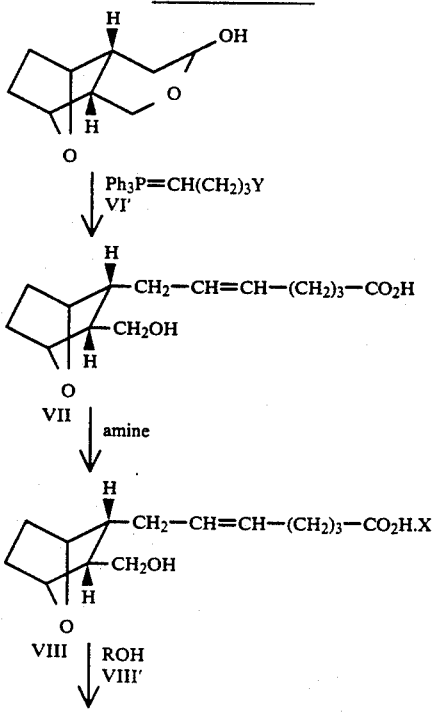

-continued
Reaction Scheme 2

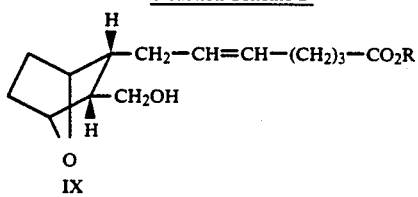

Reaction Scheme 3

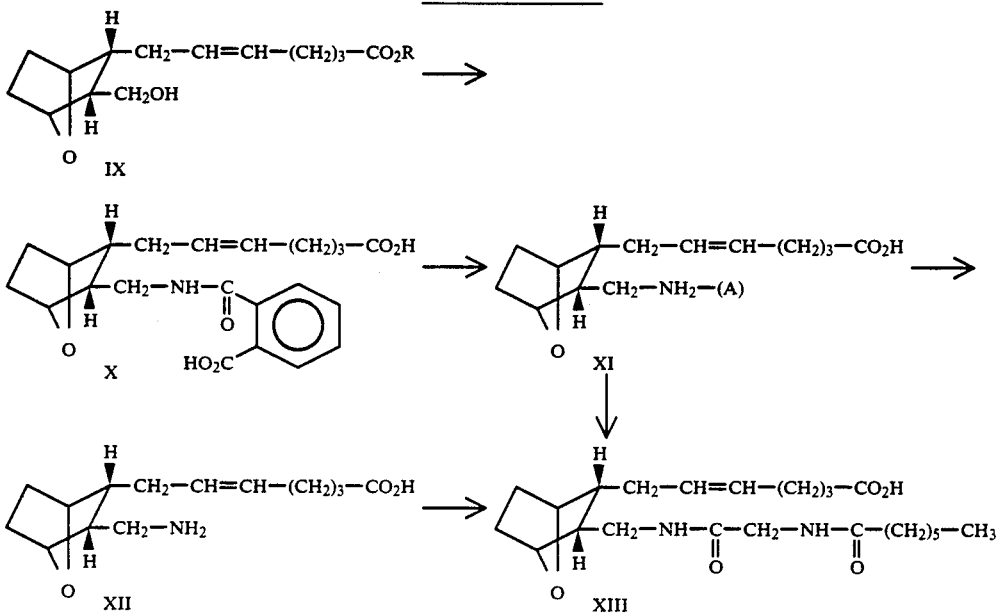

DETAILED DESCRIPTION OF THE INVENTION

The following definitions apply to the terms as used throughout this specification, both individually and as part of other groups.

The term "alkyl" or "alk-" as used herein refers to straight or branched chain hydrocarbon groups of 1 to 12 carbon atoms, preferably 1 to 6 carbon atoms.

The term "aryl" or "ar-" as used herein refers to monocyclic or bicyclic aromatic groups having from 6 to 10 carbon atoms in the ring portion, such as phenyl, naphthyl, and substituted phenyl or naphthyl having such substituents as nitro, halo, methyl or alkoxy.

The term "halogen" or "halo" refers to chlorine, bromine, and iodine.

The term "alkali metal" refers to lithium, sodium and potassium.

In Reaction Scheme 1, compounds A, B and C are converted to diol compound I by, for example, treatment with lithium aluminum hydride in tetrahydrofuran at about 35° to 45 ° C. Compound I is reacted with an acylating agent (e.g., acetic anhydride) in an organic solvent (e.g., pyridine) at about 15° to 40° C. to form compound II wherein R is alkyl, aryl, cycloalkyl, cycloalkylalkyl, aralkyl or alkaryl.

Compound II is then hydrolyzed in a selective enzymatic or microbial process. The process uses water-soluble enzymes capable of asymmetric hydrolysis to provide products in a desired enantiomeric form. Especially suitable for use with this process are the various known lipases and esterases, and Pseudomonas lipase is preferred. Pancreatin and α-chymotrypsin are also suitable. This process is able to utilize either the crude or purified forms of these enzymes in either free form or immobilized on support, while providing compounds of formula III having optical purity of 99 percent and above.

The II-to-III conversion is accomplished in a biphasic solvent system comprising an organic phase, immiscible in water, and an aqueous phase. Since the substrate (compound II) and product (compound III) are soluble in organic solvents, these compounds are contained in the organic phase of the biphasic solvent system. The water-soluble enzyme or enzymes used are contained within the aqueous phase. This process is further described in Example 1 and in the copending U.S. patent application, "(exo,exo)-7-oxabicyclo[2.2.1]-heptane-2,3-dimethanol, monoacyl ester, diacyl ester and enzymatic hydrolysis thereof" by Patel et al., filed on even date herewith, which is hereby incorporated by reference.

Thereafter, compound II wherein R: is typically methyl is oxidized to obtain the corresponding aldehydes IVA or IVB or a mixture thereof, depending on oxidation and isolation conditions. Compounds IVA and IVB, either separately or as a mixture, are hydrolyzed by treatment with, for example, an alkali metal carbonate, bicarbonate and/or hydroxide (e.g., $K_2CO_3$, $KHCO_3$, KOH) and water to form compound V in nearly pure (−) enantiomeric form. During this base hydrolysis, compound IVB epimerizes optimally above pH 10 to the cis isomer IVA or the corresponding alcohol, which cyclizes to form compound V. Intentional epimerization of compound IVA provides a mixture of compounds IVA and IVB, which upon hydrolysis and cyclization provides only compound V. These procedures are described in copending U.S. patent application, "Process for Preparing [3aR-(3aα,4β,7β,7aα)]-Octahydro-4,7-Epoxyisobenzofuranol from Associated Aldehydes", filed on even date herewith, which is hereby incorporated by reference.

Compound V is alkylated in a Wittig reaction (e.g., with $Ph_3P=CHOCH_3$ wherein Ph is phenyl), followed by aqueous acid treatment to form compound VI. Any of compounds I through VI may be conventionally hydrogenated to remove the double bond, if present.

Compound VII is prepared by treating compound VI with ylide VI' in tetrahydrofuran. When Y is $CO_2\oplus M\ominus$, it is preferred that $M\ominus$ be potassium ion. For purity, it is also preferred that oxygen be excluded by conducting the reaction in an inert atmosphere and by quenching with a nonaqueous acid. On a large scale, purity may be increased with the presence of a complexing agent such as 1,3-dimethyl-2-imidazolidinone, hexamethylphosphoramide (HMPA), or 1,3-dimethyl-3,4,5,6-tetrahydro-2(1H)-pyrimidinone (DMPU).

Compound VI' is derived preferably in situ by treating the known phosphonium salt VI" (see above) wherein halo is bromo with an alkali metal butoxide, amylate, hydride or disilazide. Potassium is the preferred alkali metal, and potassium t-butoxide, potassium t-amylate, potassium hydride and potassium hexamethyldisilazide are preferred for the respective alkali metal reagents. When Y is $-C\equiv N$, compound VI" may be prepared by reacting triphenylphosphine and $halo(CH_2)_4C\equiv N$, wherein halo is preferably bromo, in an organic solvent (e.g., toluene).

Compound VIII may be derived from compound VII by treatment with an amine (e.g., 1-adamantanamine) in an organic solvent (e.g., ethyl acetate). Crystallization of compound VIII after such treatment helps to remove the undesired trans isomer. Compound VIII then undergoes an acid-catalyzed esterification by treatment with an alcohol VIII'(e.g., methanol, ethanol, isopropyl alcohol) in the presence of an organic mineral acid (e.g., HCl) to form compound IX.

With the carboxyl group thus protected, the alcohol group may then be reacted. Compound IX is reacted with an activating reagent (e.g., triphenylphosphine-diisopropylazodicarboxylate) in the presence of phthalimide in an organic solvent (e.g., dichloromethane, toluene, or tetrahydrofuran) at about 15° to 30° C. The resulting product is reacted with a strong base such as an alkali metal hydroxide, carbonate, or bicarbonate (e.g., NaOH) at about 0° to 100° C., optionally in the presence of an organic co-solvent such as tetrahydrofuran, to form compound X.

Compound X is then hydrolyzed with water and an aqueous acid (e.g., oxalic acid) in the presence of an organic co-solvent (e.g., tetrahydrofuran) with heating to reflux (25 to 70° C., with 60° to 65° C. preferred) to form compound XI wherein A is a conjugate acid corresponding to the acid used in the hydrolysis. Mineral acids (e.g., HCl) or other organic acids (e.g., citric acid) may be employed in the hydrolysis to form compound XI. Amino acid XI is then acylated with [(1-oxoheptyl)amino]acetic acid at about 0° C. under an inert atmosphere (e.g., argon) in the presence of a coupling agent (e.g., 1,1-carbonyldiimidazole) and a tertiary amine base (e.g., N,N-diisopropylethylamine, tributylamine, or 1,8-diazabicyclo[5.4.0]undec-7-ene] to form compound XIII.

Alternatively, to reduce the trans double bond contamination from the previous Wittig reaction, compound XI may be first neutralized to compound XII by treatment with a base (e.g., triethylamine) in an organic solvent (e.g., methanol) with stirring at about 20° to 30° C. Neutralization could also be accomplished with an ion exchange resin or an inorganic base such as sodium or potassium hydroxide, carbonate, or bicarbonate. Like compound XI, compound XII is finally acylated with [(1-oxoheptyl)amino]acetic acid to form compound XIII.

The invention will now be further described by the following working examples, which are illustrative rather than limiting. These examples constitute preferred embodiments of the invention.

EXAMPLE 1

[1S-[1α,2β(5Z),3β,4α]]-7-[3-(Hydroxymethyl)-7-oxabicyclo[2.2.1]hept-2-yl]-5-heptenoic acid, methyl ester 1-A. (exo,exo)-7-Oxabicyclo[2.2.1]heptane-2,3-dimethanol Lithium aluminum hydride pellets (about 27.3 g) were added portionwise to a solution of tetrahydrofuran (about 1 L) under argon. After stirring for 0.5 hours, (3aα,4β,7β,7Aα)hexahydro-4,7-epoxy-isobenzofuran-1(3H)-one (50.0 g) was added portionwise and at such a rate as to maintain the internal temperature around 40° C. The suspension was then stirred at ambient temperature for 22 hours.

The reaction was quenched by the slow dropwise addition of $H_2O$ (32 mL), 15% NaOH (32 mL), and $H_2O$ (90 mL). After stirring for one hour, the white precipitate was filtered, and the solids washed with tetrahydrofuran (2×50 mL). The combined, filtrates were dried (magnesium sulfate), filtered and concentrated to a yellow oil that solidified on standing. Ether (50 mL) was added and the mixture was allowed to stand at 0° C. for 16 hours. After filtration, the solids were triturated with hexanes. Filtration and drying then afforded 50.8 g (99%) of diol 1-A.

1-B. (exo,exo)-7-Oxabicyclo[2.2.1]heptane-2,3-dimethanol, diacetate ester

Acetic anhydride (50 mL) was added to a solution of diol 1-A (16.9 g) in pyridine (100 mL). The internal temperature increased to approximately 30° C. The reaction was then left at room temperature for 20 hours.

The solution was concentrated and then co-evaporated several times with toluene/methanol to remove the acetic anhydride and pyridine. Ethyl acetate (250 mL) was added and the solution was extracted with 0.5% aqueous HCl (1×50 mL), $H_2O$ (1×50 mL), saturated aqueous $NaHCO_a$ (2×50 mL), and saturated brine (3×50 mL). The organic phase was dried ($MgSO_4$), filtered, and concentrated to a solid. Trituration with hexanes and filtration afforded diacetate 1-B (23.3 g, 90% yield) as a white crystalline solid.

1-C. (−)-(exo,exo)-7-Oxabicyclo(2.2.1) heptane-2,3-dimethanol, monoacetate ester

Method I

An enzyme solution was prepared by mixing 4 g (120,000 units) of crude Pseudomonas lipase P-30 (Amano International, USA) in 200 mL of 50 mM phosphate buffer, pH 7.0. The pH was checked and adjusted to 7.0 with 2 N sodium hydroxide. The suspension was centrifuged at 10,000 RPM for 15 minutes at 4° C. to remove insoluble materials. The recovered supernatant was cooled to 4° C., to be ready for use below.

To 50 mM phosphate buffer (600 mL, pH 7.0) was added toluene (200 mL) containing 2 g of diester 1-B. The so-formed emulsion of toluene in buffer was then cooled to and maintained at 5° C. The 200 mL of 50 mM phosphate buffer, pH 7.0 containing 5 g (150,000 units) of the crude Pseudomonas P-30 lipase was then introduced to the solution while continuing the agitation at 200 RPM. The reaction was allowed to continue for 47 hours and the pH was maintained at 7.0 by the addition, as necessary, of 2.5 N sodium hydroxide using a pH stat. During reaction, at various time intervals, 5 mL samples were taken, extracted with 5 volumes of ethyl acetate (25 mL). The ethyl acetate layers were separated and evaporated to dryness to obtain an oily residue containing the title compound. The amount of substrate 1-B and product 1-C was analyzed by gas chromatography. The optical purity of the product was determined by chiral HPLC.

After completion of the hydrolysis (47 hours), the reaction mixture was extracted with 5 volumes of ethyl acetate (5 liters) and the ethyl acetate layer was separated from aqueous layer. The ethyl acetate layer was evaporated under vacuum to yield 1.3 grams of the title compound with an (−) enantiomeric purity of 96.8% (Table 1).

The procedures of Method I were carried out under the parameters defined below.

Method II

Enzyme: Pseudomonas lipase (Biocatalyst, UK)
Biphasic solvent: 4 mL toluene, 36 mL of 50 mM phosphate buffer, pH 7.0
Sustrate 2 mg compound 1-B/mL biphasic solvent
Enzyme per substrate: 10 mg/mg of substrate
Temperature: 4° C.

Method III

Enzyme: Pseudomonas lipase (Amano International, USA)
Biphasic solvent: 4 mL toluene, 36 mL of 50 mM phosphate buffer, pH 7.0
Substrate: 2 mg compound 1-B/mL biphasic solvent
Enzyme per substrate: 10 mg/mg of substrate
Temperature: 4° C.

Method IV

Enzyme: Pseudomonas lipase (Squibb, USA)
Biphasic solvent: 8 mL toluene, 32 mL of 50 mM phosphate buffer, pH 7.0
Substrate: 2 mg compound 1-B/mL biphasic solvent
Enzyme per substrate: 10 mg/mg of substrate
Temperature: 4° C.

Method V

Crude Pseudomonas lipase P-30 (500 g) was dissolved in 2600 mL of deionized water and centrifuged at 12,000 RPM for 20 minutes to remove insoluble materials. The clear supernatant solution, was added to 50 grams of Accurel polypropylene (Enka Industrial Products, Co., USA) which was previously washed with methanol. The enzyme and carrier (Accurel Polypropylene) slurry was incubated at 28° C. for 24 hours at 150 RPM on a shaker. Immobilized lipase on Accurel polypropylene was filtered and washed with water. The resins were then dried under vacuum at 25° C. for 24 hours. About 56 grams of immobilized lipase on Accurel polypropylene was obtained.

Reaction was conducted in a 5-liter jacketed reactor. The reactor contained 2.7 liters of 50 mM phosphate buffer, pH 7.0 containing 7.5 grams of Pseudomonas lipase P-30 (Amano International, USA) immobilized on Accurel polypropylene as described above. The reaction was started by addition of 300 mL of toluene containing 15 g of substrate 1-B. The reaction was carried out at 5° C., 200 RPM agitation, and pH 7.0 (maintained by 5.25 N NaOH with a pH stat). Based upon analysis by gas chromatography, 89 M% conversion of substrate 1-B to product 1-C was achieved after 26 hours (Table 2).

Another 3-liter batch was conducted following the above procedures. After 27.5 hours of hydrolysis, 82 M% conversion of substrate diacetate ester to product (−)monoacetate ester was obtained. Both batches, containing a total 6-liter reaction mixture, were used for recovery and crystallization of (−)-(exo,exo)-7-oxabicyclo (2.2.1)heptane-2,3- dimethanol monoacetate ester as follows.

The above-named monoacetate ester product from the 6-liter reaction was extracted with 30 liters of ethyl acetate. The ethyl acetate extract was separated and concentrated to obtain 27 grams of oily materials. The concentrates were placed at 7° C. overnight, and the oily solids were washed with hexane (3×100 mL). The solids were then dissolved in 100 mL of methylene chloride, with subsequent addition of 100 mL of hexane. Crude crystals were formed upon the concentration of the solution under reduced pressure. The crude crystals were separated from the mother liquor and recrystallized in a 1:1 methylene chloride and hexane mixture to yield white crystals (14 g) with a 99.5% optical purity (chiral HPLC and NMR analysis). Gas chromatography of the preparation gave 99.5% HI. Thin layer chromatography (Rf=0.46, ethyl acetate:hexane, 70:30, v/v), melting point 80.5° C.

The procedures of Method V were followed

Method VI

Enzyme: Immobilized Pseudomonas lipase (Biocatalyst, UK)
Biphasic solvent: 4 mL toluene, 36 mL of 50 mM phosphate buffer, pH 7.0
Substrate: 2 mg compound 1-B/μL biphasic solvent
Enzyme per substrate: 0.5 mg of immobilized enzyme/mg of substrate
Temperature 4° C.

Method VII

Enzyme: Immobilized Pseudomonas lipase (Amano International, Co. USA)
Biphasic solvent: 4 mL xylene, 36 mL of 50 mM phosphate buffer, pH 7.0
Substrate 2 mg compound 1-B/mL biphasic solvent
Enzyme per substrate: 0.5 mg of immobilized enzyme/mg of substrate
Temperature 4° C.

Method VIII

Enzyme: Immobilized Pseudomonas lipase (Amano International, Co. USA)
Biphasic solvent: 8 mL toluene, 32 mL of 50 mM phosphate buffer, pH 7.0
Substrate: 2 mg compound 1-B/mL biphasic solvent
Enzyme per substrate: 0.5 mg of immobilized lipase/mg of substrate
Temperature: 4° C.

Method IX

Enzyme: Immobilized Pseudomonas lipase (Amano P-30) on Accurel-pp bead (200 g)
Biphasic solvent: 8 L toluene, 72 L of 0.05 M potassium phosphate solution
Substrate: 400 g compound 1-B Temperature: 5±0.5° C.

1-D. [1S-(1α,2α,3α,4α)]-3-[(Acetyloxy)methyl]-7-oxabicyclo[2.2.1]heptane-2-carboxaldehyde A solution of oxalyl chloride (3.8 mL, 43.56 mmol) in dichloromethane (125 mL) was cooled to −60° C. under argon. A solution of dimethylsulfoxide (8.0 mL, 112.7 mmol) in dichloromethane (20 mL) was added dropwise over 15 minutes while maintaining the internal temperature at −60° C. The solution was stirred another 15 minutes at −60° C.

A solution of compound 1-C (5.1 g, 25.28 mmol, 99.3% optical purity by chiral shift NMR) in dichloromethane (20 mL) was added dropwise over 10 minutes at −60° C. The resulting cloudy mixture was stirred another 20 minutes at −60° C. Diisopropylethylamine (37 mL, 212.41 mmol) was added dropwise over 25 minutes at −60° C. The resulting clear solution was warmed to −45° C. and stirred until no starting material was left by TLC (about 35 additional minutes).

The reaction was quenched by the addition of 125 mL of 10% HCl to the solution. After the solution froze, the cooling bath was removed and the mixture was stirred until completely melted and then for an additional 45 minutes.

The solution was transferred to a separatory funnel and the layers were separated. The aqueous phase was extracted with dichloromethane (2×50 mL). The combined organic layers were washed with 10% HCl (2×100 mL), water (1×50 mL), saturated NaHCO$_3$ (1×75 mL), and saturated NaCl (2×100 mL). The organic layer was dried over magnesium sulfate, then filtered and concentrated in vacuo to 5.45 g of a crude yellow solid (110%). The crude product was stirred in hexane, filtered and dried in vacuo to produce 5.1 g of cis-aldehyde 1-D (96%), melting point 39.0°–41.5° C.

1-E. [3aR-(3aα,4β,7β,7aα)]-Octahydro-4,7-epoxyisobenzofuran-1-ol

Solid potassium carbonate was added to a room temperature suspension of aldehyde 1-D (3.654 g, 18.45 mmol) in water (30 mL) to adjust the pH to 11. The solution was maintained at pH 10.95 to 11.10 with additions of 40% KOH (w/v) until the hydrolysis was complete by TLC.

The solution was neutralized with glacial acetic acid added in small portions to control foaming. Solid NaCl was added and stirred in order to saturate the solution. The solution was filtered to remove excess solid NaCl. The solution was extracted with 10% acetonitrile in ethyl acetate (15×20 mL). The organic layers were combined, dried over magnesium sulfate, filtered, and concentrated in vacuo to 2.65 g (95%) of crude yellow solid.

A portion of the crude product (0.98 g) was purified by dissolving it in 1 mL of dichloromethane, followed by the addition of cold cyclohexane (4×1 mL) with stirring. Upon addition of the fourth milliliter of cyclohexane, the product immediately crystallized. After refrigeration overnight, the solid was filtered, washed with hexane, and dried in vacuo to give 0.65 g (66%) of compound 1-E.

1-F. (±)-(exo,exo)-7-Oxabicyclo(2.2.1)heptane-2,3-dimethanol, monoacetate ester

Sodium hydride (835 mg, 20.9 mmol) was added portionwise to a solution of compound 1-A (3.0 g, 19.0 mmol) in tetrahydrofuran (100 mL) at room temperature. After stirring for 4 hours, the mixture was cooled to −10° C. and acetyl chloride (1.55 mL, 21.9 mmol) was added. The reaction was then allowed to warm to ambient temperature and stirred for an additional 16 hours. Acetic acid (0.25 mL) was added, followed by Celite (2 g). The suspension was then filtered through Celite with the residual solids being washed with additional tetrahydrofuran. The combined filtrates were concentrated to a semi-solid and applied to a silica gel column. Elution using ether-hexanes (1:1) afforded the monoacetate 1-F (2.32 g, 61% yield) as a clear colorless oil that slowly crystallized on standing.

1-G. (±)-(1α,2α,3α,4α)-3[(Acetyloxy)methyl]-7-oxabicyclo[2.2.1]heptane-2-carboxaldehyde A solution of oxalyl chloride (60 mL) in dichloromethane (2000 mL) was cooled to −60° C. and was treated with stirring over 15 minutes with a solution of dimethylsulfoxide (DMSO) (124 mL) in dichloromethane (300 mL). The solution was stirred for 15 minutes at −60° C.

A solution of compound 1-F (80 g) in dichloromethane (500 mL) was added over 10 minutes and the reaction was stirred for an additional 30 minutes. Diisopropylethylamine (600 mL) was added over five minutes at −60° C. Cooling was removed and the temperature rose to 45° C. over 10 minutes. The cold mixture was added to 2000 mL of ice water under stirring.

The organic layer was separated and the aqueous layer was extracted two times with 500 mL dichloromethane. The combined organic layers were extracted with 10% hydrochloric acid (1400 mL), water (600 mL), saturated sodium hydrogen carbonate (1200 mL) and brine (1000 mL). The organic phase was dried over magnesium sulfate, filtered and concentrated to a syrup that solidified on standing. The solids were broken up, stirred with 50 mL hexane, filtered and dried to give the title compound, 78.5 g (99%) corrected for water, melting point 43°–44° C., with about 30% trans isomer IVB ($R^1$=CH$_3$).

TLC: Ethyl acetate, R$_f$ 0.5, visualization ammonium molybdate/ceric sulfate.

1-H. (±)-(3aα,4β,7β,7aα)-Octahydro-4,7-epoxyisobenzofuran-1-ol

The product from 1-G above (80 g) was dissolved in 392 mL water. A small amount of solids remained undissolved. The mixture was treated with 70 mL hexanes, stirred, and filtered, and the layers were separated. The pH was 2.32. The aqueous layer was treated dropwise under nitrogen with 50% sodium hydroxide to maintain pH 10.8 to 11.0. 20.9 mL were added over 6 hours.

The pH 11.0 solution was neutralized to pH 7.0 with 1.6 mL glacial acetic acid and was saturated with solid sodium chloride. After stirring for 15 minutes, the aqueous solution was extracted with 10% acetonitrile in ethyl acetate (12×350 mL). The combined organic extracts were dried over magnesium sulfate and then were concentrated to dryness. A soft crystalline solid was obtained. The solids were triturated with 75 mL ethyl ether, filtered and dried. 54 g of the title compound were obtained, 85.5% yield, melting point 123°–124° C.

1-I. [4aR-(4aα,5β,8β,8aα)]-Octahydro-5,8-epoxy-1H-2-benzopyran-3-ol

A slurry of methoxymethyltriphenylphosphonium chloride (1.09 kg, 3.18 mol) in Burdick and Jackson sieve-dried tetrahydrofuran (3 liters) was chilled to 0° C. and treated dropwise with 1.4 M potassium t-amylate in toluene (1910 mL, 2.67 mol) over twenty minutes. The resultant dark red solution was stirred at 0° C. for one hour. The mixture was then treated slowly over five minutes with solid [3aR-(3aα,4β,7β,7aα)]-Octahydro-4,7-epoxyisobenzofuran-1-ol (200 g, 1.28 mmol), which may be prepared as described in part 1-E above or by resolving racemic compound 1-H by art-recognized procedures. The temperature gradually rose to 23° C. The mixture was stirred vigorously at room temperature for ninety minutes. The reaction mixture was then chilled to 0° C. and treated slowly with acetaldehyde (124 mL, 2.2 mol) over ten minutes. The mixture was diluted with water (2500 mL) and treated with 10% hydrochloric acid to pH 7. The mixture was then extracted with ether and stirred overnight The mixture was chilled to −10° C. for nlninety minutes and then filtered. The solids were washed thoroughly with isopropyl ether. The filtrate was concentrated in vacuo to an oily residue (460 g). This oily residue was treated with water (4000 mL) and stirred vigorously for two hours. The aqueous layer was decanted and the oily residue treated two additional times with water (2×1 liter). After the third wash, the residue solidified and was filtered. The combined aqueous triturates were concentrated in vacuo to 3.5 liters. The cloudy mixture was filtered through a bed of Celite. The filtrate was concentrated again to a volume of 2.3 liters. The cloudy solution was chilled in an ice bath and treated slowly with concentrated hydrochloric acid (683 mL). The mixture was then stirred at room temperature for three hours. After this time the solution was neutralized by the slow addition of solid sodium bicarbonate (720 g). The mixture was filtered through a bed of Celite and extracted first with hexane (4×2 liters), then with ethyl acetate (10×2 liters). The combined ethyl acetate extracts were dried over MgSO4 and concentrated in vacuo. The solid residue was triturated with hexane (1 liter), filtered and dried in vacuo to yield 220 g (100%) of the title compound. Melting point 104°-105° C., [α]$_D^D$=+27° c=1, methanol. TLC: Silica gel; ethyl acetate; R$_f$=0.3; Ce(SO4)2.

1-J. [1R-[1α,2α(Z),3α,4α]]-7-[3-(Hydroxymethyl)-7-oxabicyclo[2.2.1]hept-2-yl]-5-heptenoic acid, 1-adamantanamine (1:1) salt A 500-mL, 3-necked flask equipped with argon inlet, thermometer and overhead stirrer was charged with 150 mL of a 1 M tetrahydrofuran solution of potassium tert-butoxide (Aldrich) and cooled to an internal temperature of −2° C. (4-Carboxybutyl)triphenylphosphonium bromide (32.867 g, 74.14 mmol; dried in vacuo at 100° C. overnight) was added in portions over 15 minutes while maintaining an internal temperature of 0°-5° C. The resulting orange-red mixture was stirred at 0° C. for an additional 15 minutes and then at ambient temperature for 2 hours. The red mixture was then cooled to −72° C. and treated, via cannula, over 15 minutes with a chilled (−30° C.) solution of R-enantiomer 1-I (5.862 g, 34.48 mmol) in 55 mL of distilled tetrahydrofuran. The reaction was allowed to stir while warming slowly (cooling bath in place) to room temperature. Solid lithium bromide (6 g, 68.96 mmol) was added, the reaction was stirred an additional 1.5 hours and cooled to 0° C. While maintaining the internal temperature at ≦10° C., 50 mL of 3 M hydrochloric acid was added. The mixture was further diluted with 100 mL of water followed by 150 mL of ethyl acetate.

After transferring to a separatory funnel, the layers were separated and the aqueous layer extracted with additional ethyl acetate (3×70 mL). The combined organic extracts were washed with 60 mL of 1 M hydrochloric acid, 60 mL of water and then with saturated sodium bicarbonate solution (2×150 mL, 3×5 mL). The product-rich basic extracts were washed with ethyl acetate (2×100 mL) and acidified to pH 2 with concentrated hydrochloric acid. The acidic mixture was extracted with dichloromethane (2×150 mL, 2×50 mL). The organic extracts were washed with brine, dried over sodium sulfate and filtered. The filtrate was concentrated in vacuo to an orange oil that was evaporated from ethyl acetate (2×100 mL) to a very heavy slurry (22.5 g). Additional ethyl acetate (97 mL) was added and the mixture was heated to dissolve suspended material. The resulting slurry was cooled to room temperature and stirred overnight. 5-(Diphenylphosphinyl)pentanoic acid was removed by filtration and washed with ethyl acetate. The filtrate was concentrated in vacuo to 9.611 g of crude [1R-[1α,2α(Z),3α, 4α]]-7-[3-(hydroxymethyl)-7-oxabicyclo2.2.1]-hept-2-yl]-5-heptenoic acid.

A 3-necked, 1 L flask equipped with overhead stirrer, and reflux condensor capped with nitrogen inlet was charged with a solution of the above crude product in warm ethyl acetate (185 mL). A solution of 1-adamantanamine was prepared separately by slurrying 6.98 g (46.05 mmol) in 150 mL of ethyl acetate followed by filtration, concentration in vacuo to a solid and addition of ethyl acetate (145 mL). The amine solution was then added to the solution of crude product (slight exotherm) resulting in the formation of a precipitate.

Methanol (30 mL) was added and the suspension was heated to reflux. Additional methanol was added through the condensor until a clear solution was obtained (40 mL required). Solvent was then allowed to distill off until the solution developed a haze and a small amount of solid was evident. The flask was closed and 3.5 mL of methanol was added through a condenser. The flask was cooled slowly and stirred overnight. The product was filtered and washed with ethyl acetate and hexane and dried under high vacuum. The yield was 11.349 g (81%), 1.1% trans isomer produced.

The foregoing procedure may be repeated with the S-enantiomer under the same conditions.

1-K. [1S-[1α,2α(Z),3α,4α]]-7-[3-(Hydroxymethyl)-7-oxabicyclo[2.2.1]hept-2-yl]-5-heptenoic acid, 1-adamantanamine (1:1) salt To a 2-liter, 3-necked, round bottom flask maintained under a nitrogen atmosphere and equipped with a mechanical stirrer and two addition funnels was charged (4-carboxybutyl)triphenylphosphonium bromide (130.3 g, 294.1 mmol, Aldrich), tetrahydrofuran (50 mL) and 1,3-dimethyl-3,4,5,6-tetrahydro-2(1H)-pyrimidinone (DMPU) (71.15 mL, 588.4 mmol). To an addition funnel was charged the S-enantiomer of compound 1-1 (25.0 g, 147.1 mmol) and tetrahydrofuran (200 mL). The flask was cooled to 0° C. and a solution of 1 M potassium t-butoxide in tetrahydrofuran (588.5 mL, 588.5 mmol) was added rapidly via the second addition funnel, which was subsequently replaced with an internal thermometer. The reaction mixture was stirred at 0° C. for 0.5 hours and then the cooling bath was removed for 1 hour, final temperature 21° C. The flask was cooled to 0° C. and slowly over 70 minutes was added the S-enantiomer solution and the addition funnel was rinsed with an additional 25 mL tetrahydrofuran. Completion of the reaction was determined by thin layer chromatography (8:1 methylene chloride/methanol) as soon as the rinse was complete. The reaction was quenched 15 minutes after the rinse by the rapid addition of acetic acid via syringe.

The reaction was allowed to warm to room temperature. Water (1500 mL) and ethyl acetate (750 mL) were added at pH 5.77. The pH was adjusted to 13.0 by the slow addition of 10 N sodium hydroxide (51 mL) and fell to 10.72 in 5 minutes. The phases were split and the rich aqueous phase was washed with 1×750 mL ethyl acetate and 1×750 mL of methyl isobutyl ketone (MIBK). (Tetrahydrofuran may be removed by vacuum-distillation.) To the rich aqueous phase was added MIBK (750 mL) and concentrated hydrochloric acid (100 mL) to pH 0.88. This mixture was stirred for 10 minutes, the phases were split, and the aqueous phase was extracted with an additional 500 mL of MIBK. The MIBK layers were combined and washed with water [1×500 mL, 1×300 mL with 200 mL brine and 25 mL ethanol]. It took about 12 hours of settling time to effect a clean phase split.

The MIBK-rich phase was placed in a 3-necked., 5-liter round bottomed flask equipped with an overhead stirrer, internal thermometer and still head. The MIBK was dried via azeotropic distillation of about 16 to 20" Hg at 50° to 60° C. to dryness (by KF), with a reduction in volume of 500 mL. (Acetic acid may be removed by co-distillation with MIBK.) 1-Adamantanamine in MIBK (250 mL and a rinse of 100 mL) was charged via vacuum filtration to the hot solution. The solution was heated to reflux (118° C.) and additional MIBK (150 mL) was added as needed to achieve dissolution. The solution was reduced in volume via distillation to a crystallization volume of about 1400 mL (calculated by high pressure liquid chromatography (HPLC)). The solution was allowed to cool slowly and crystallization was observed at 90° C. The slurry was held for 1 hour at 90° C., 1 hour at 60° C., then allowed to cool slowly to 22° C. and held for 14 hours with stirring. The product was isolated on a 9-cm buchner funnel, washed (2×125 mL) with MIBK, and dried on a filter for 0.5 hours and in vacuo at 40° C. for 5 hours. This procedure provide 26.03 g (84% recovery) of essentially 100% pure compound 1-J.

The foregoing procedure may be repeated with the R-enantiomer under the same conditions.

1-L. [1S-[1α,2α(5Z),3β,4α]]-7-[3-(hydroxy-methyl)-7-oxabicyclo[2.2.1]hept-2-yl]-5-heptenoic acid, methyl ester Acetyl chloride (93.9 mL, 1.33 mol) was slowly added to 2.2 L of methanol at 0° C. The resulting solution was stirred for 30 minutes. Solid compound 1-K was added and the reaction was stirred and allowed to warm to room temperature over 5 hours. (To form the associated R-enantiomer, compound 1-J may be used.) The reaction was cooled to 5° C. and triethylamine (38.6 mL, 28 mmol) was added. The mixture was stirred an additional 10 minutes and concentrated in vacuo. The residue was treated with 2L of water, the pH was adjusted to 2.6, and ethyl acetate (1.5L) was added. The mixture was shaken and the layers were separated; the aqueous layer was then extracted with additional ethyl acetate (2×1.5 L). The organic extracts were washed with water, saturated bicarbonate solution, water and brine. The organic solution was dried (magnesium sulfate), filtered and concentrated in vacuo to 289.6 g (97%) of the title compound.

EXAMPLES 2 TO 18

[1R-[1α,2β(5Z),3β,4α]]-7-[3-(Hydroxymethyl)-7-oxabicyclo[2.2.1]hept-2-yl]-5-heptenoic acid, methyl ester The following examples employed the procedures of Example 1, except that steps 1-J and 1-L were carried out under the conditions described below. In each example, the ylide was formed using the noted base as in step 1-J and then condensed with the lactol as in step 1-L at the noted temperature. For the condensation, the reaction temperature initially was set as shown below and then allowed to warm to room temperature.

| Ex. | Equiv. 2-A. | Equiv. Base | Solvent | Temp. | % trans isomer (by HPLC) |
|---|---|---|---|---|---|
| 2 | 1.5 | 2.89 potassium-tert-amylate | toluene | 0° C. | 9.1 |
| 3 | 2.1 | 4.2 potassium-tert-amylate | toluene | −78° C. | 7.22 |
| 4 | 2.1 | 4.2 potassium-tert-amylate | toluene-DMF (60%) | −78° C. | 7.45 |
| 5 | 2.15 | 4.3 potassium-tert-amylate/DBU (1.1 equiv) | toluene | −78° C. | 6.65 |
| 6 | 1.2 | 3.4 potassium hexamethyldisilazide | toluene | −78° C. | 9.55 |
| 7 | 2.15 | 4.35 lithium hexamethyldisilazide | THF | −78° C. | 25 |
| 8 | 1.5 | 4.1 sodium hexamethyldisilazide | THF | −78° C. | 7.9 |
| 9 | 2.1 | 4.2 sodium hexamethyldisilazide | THF | −78° C. | 8.05 |
| 10 | 1.5 | 4.2 potassium hexamethyldisilazide | THF | −78° C. | 4.7 |
| 11 | 2.15 | 4.35 potassium hexamethyldisilazide | THF | −78° C. | 4.4 |
| 12 | 2.15 | 4.3 potassium-tert-butoxide | THF | −78° C. | 4.2 |
| 13 | 1.5 | 4.2 potassium-tert-butoxide | THF | −78° C. | 4.85 |
| 14 | 2.15 | 4.35 potassium-tert-butoxide | THF-DMF (44%) | −78° C. | 4.1 |
| 15 | 2.15 | 4.3 potassium-tert-butoxide/DBU (1.1 equiv) | THF | −78° C. | 4.15 |
| 16 | 2.15 | 4.3 potassium-tert-butoxide | THF-DMPU (15%) | −78° C. | 4.44 |
| 17 | 2.15 | 4.3 potassium hydride | THF-DMF (6%) | −78° C. | 7.7 |
| 18 | 2.15 | 4.35 sodium hydride | DMF | −50° C. | 14 |

"DBU" refers to 1,8-diazabicyclo[5.4.0]undec-7-ene;
"DMF" refers to dimethylformamide;
"DMPU" refers to 1,3-dimethyl-3,4,5,6-tetrahydro-2(1H)-pyrimidinone;
"THF" refers to tetrahydrofuran.

isolated 38.87 g (65.1%) of 99.0% pure compound 2-A containing 0.4% trans isomer.

A portion of the first crop of this product (35.0 g) was recrystallized from MIBK (880 mL) to afford 33.29 g (95% recovery) containing 0.3% trans isomer, and 0.4% of an impurity. A second recrystallization was performed using 31.0 g of the recrystallized material using methanol (50 mL) and ethyl acetate (250 mL) to

EXAMPLE 19

1R-[1α,2α(5Z),3α,4α]]-7-[3-(Hydroxymethyl)-7-oxabicyclo[2.2.1]hept-2-yl-5-heptenoic acid, 1-adamantanamine (1:1) salt 9-A. 4-(Cyanobutyl)triphenylphosphonium bromide A solution of triphenylphosphine (58 g, 0.221 mol) and 5-bromovaleronitrile (31.078 g, 0.192 mol) in toluene (315 mL) was stirred at 105° C. (bath temperature) under argon for 5 days. The flask was cooled to room temperature, and the product was filtered and washed with 300 mL of toluene followed by 200 mL of hexane. The crude product was reslurried in hexane (200 mL), filtered and washed with an additional 300 mL of hexane. Drying under high vacuum produced 63.515 g of the title compound. (78%).

Analysis for $C_{23}H_{23}BrNP$: Calc'd: C,65.10; H,5.46; N,3.30. Found: C,65.06; H,5.57; N 3.38.

19-B. [1R-[1α,2α(5Z),3α,4α]]-7-[3-(Hydroxymethyl)-7-oxabicyclo[2.2.1]hept-2-yl]-5-heptenenitrile A 500-mL, 3-necked flask equipped with argon inlet, thermometer and overhead stirrer was charged with 4-(cyanobutyl)triphenylphosphonium bromide (31.835 g, 74.99 mmol) and 130 mL of distilled tetrahydrofuran. The suspension was cooled to −60° C. and treated slowly (over 15 minutes) with a solution of potassium tert-butoxide (75 mL of a 1 M solution) in tetrahydrofuran. The resulting mixture was stirred at −50° to −55° C. for 3 hours. During this time, the reaction mixture becomes orange in color. The reaction mixture was cooled to −70° C. and treated, via cannula over 20 minutes, with a chilled (−30° C.) solution of R-enantiomer 1-I (5.95 g, 34.88 mmol) in 35 mL of distilled tetrahydrofuran. Residual lactol 1-I was rinsed through the cannula with two 15 mL portions of tetrahydrofuran. The reaction was allowed to stir while warming slowly (over about 14 hours, cooling bath in place) to room temperature. While maintaining the internal temperature at less than 15° C., 50 mL of 3 M HCl was added. The mixture was further diluted with 100 mL of water followed by 150 mL of ethyl acetate. After transferring to a separatory funnel, the layers were separated and the aqueous layer extracted with additional ethyl acetate (3×70 mL). The combined organic extracts were washed with 60 mL of 1 M HCl, 60 mL of saturated sodium bicarbonate solution and 60 mL of brine and dried over sodium sulfate. Filtration followed by concentration in vacuo produced an orange oil that was redissolved in about 200 mL of ethyl acetate and treated with 1 g of Norit. The resulting mixture was stirred at room temperature for 2 hours, filtered and concentrated in vacuo to an oil.

19-C. [1R-1α,2α(Z),3α,4α]]-7-[3-(hydroxymethyl)-7-oxabicyclo[2.2.1]hept-2-yl]-5-heptenoic acid A solution of crude Wittig reaction mixture from above in 120 mL of absolute ethanol was treated with a solution of potassium hydroxide (39 g, 0.7 mol) in 400 mL of water. The resulting mixture (some insoluble material) was stirred at reflux (bath temperature 120° C.) under nitrogen for 24 hours, cooled and diluted with water (150 mL). The pH was lowered from 12.4 to 8.0 with concentrated HCl (47 mL required) and the mixture washed with ethyl acetate (4×100 mL). The product-rich aqueous layer was acidified to pH 2 with concentrated HCl and extracted with dichloromethane (4×100 mL). The extracts were washed with brine and dried over sodium sulfate. Filtration followed by concentration in vacuo produced 18.5 g of solid composed of the title compound, 5-(diphenylphosphinyl)pentanoic acid, and diphenylphosphinic acid. The crude product was slurried in 125 mL of boiling ethyl acetate, cooled to room temperature and stirred overnight. 5-(Diphenylphosphinyl)pentanoic acid and diphenylphosphinic acid were removed by filtration and washed with ethyl acetate. The filtrate was concentrated in vacuo to 10.13 g of crude title compound,(3.67% trans-double bond isomer by HPLC).

19-D. [1R-[1α,2α(Z),3α,4α]]-7-[3-(hydroxymethyl)-7-oxabicyclo[2.2.1]hept-2-yl]-5-heptenoic acid, 1-adamantanamine (1:1) salt A 3-necked, 1-L flask equipped with overhead stirrer and reflux condenser capped with nitrogen inlet was charged with a solution of crude [1R-[1α,2α(Z),3α,4α]]-7-[3-(hydroxymethyl-7-oxabicyclo[2.2.1]hept-2-yl]-5-heptenoic acid in ethyl acetate-methanol (200 mL:34 mL). A solution of 1-adamantanamine was prepared separately by slurrying 7.733 g (51.2 mmol) in 170 mL of ethyl acetate, followed by filtration, concentration in vacuo to a solid, and addition of ethyl acetate (160 mL). The amine solution was then added to the above heptenoic acid solution, followed by 44 mL of methanol. The resulting suspension was heated to reflux to afford a clear, yellow solution. Solvent was then allowed to distill off until only a small amount of solid was visible. The flask was closed and 8 mL of methanol was added through the condenser. The flask was cooled slowly (overnight) with stirring. The product was filtered and washed with ethyl acetate and hexane and dried under high vacuum. The yield of the title compound was 11.296 g (75% from 19-B; 0.88% trans-double bond isomer by HPLC).

EXAMPLE 20

The procedures of Example 19 were repeated using potassium hexamethyldisilazide instead of potassium t-butoxide in step 19-B. This procedure resulted in 2.3% trans isomer of acid 19-C.

EXAMPLE 21

[1S-[1α,2α(Z),3α,4α]]-7-[3-[[[[(1-oxoheptyl)amino]-acetyl]amino]methyl-7-oxabicyclo[2.2.1]hept-2-yl]-5-heptenoic acid 21-A. [1S-[1α,2α(Z),3α,4α]]-7-oxabicyclo[2.2.1]-hept-2-yl]-5-heptenoic acid, oxalate (1:1) salt A dry 500-mL flask equipped with stirrer, argon (nitrogen) inlet, thermometer and dropping funnel was charged with [1S[1α,2α(Z),3α,4α]]-7-[3-hydroxymethyl) -7-oxabicyclo[2.2.1]hept-2-yl]-5-heptenoic acid, methyl ester (20.007 g, 74.65 mmol, triphenylphosphine (22.518 g, 85.85 mmol) and dichloromethane (270 mL from a freshly or recently opened bottle). After stirring several minutes to obtain a clear solution, finely ground phthalimide (12.082 g, 82.12 mmol) was added. While maintaining the internal temperature at about 20° to 25° C. with a water bath, a solution of diisopropylazodicarboxylate (16.907 g, 93.61 mmol) in dichloromethane (45 mL) was added dropwise over 30 minutes. After the addition, the reaction was stirred at room temperature for 4 hours.

The solvent was removed in vacuo to a heavy oil which was dissolved in toluene (450 mL). The resulting solution was washed with ice cold 0.25 M NaOH (3×80 mL), cold water (1×80 mL) and brine (1×80 mL). The toluene solution was dried over sodium sulfate, filtered and concentrated to a heavy oil, which was dissolved in tetrahydrofuran (350 mL) and treated (under argon) via a dropping funnel with a solution of lithium hydroxide monohydrate (10.964 g, 261.29 mmol) in 260 mL of distilled water. The reaction was vigorously stirred under argon for 2 hours and acidified to pH 9.6 with about 20 mL of concentrated hydrochloric acid (added dropwise over about 15 minutes).

The reaction was transferred to an evaporating flask and 331 mL of solvent was removed in vacuo at ≦30° C. Ethyl acetate (250 mL) was immediately added to the residue and the mixture was transferred to a separatory funnel and shaken. The organic layer was discarded and the aqueous layer was washed with additional ethyl acetate (3×250 mL).

The product-rich aqueous layer was stirred while adjusting the pH from 8.8 to 7 with several drops of concentrated hydrochloric acid. Ethyl acetate (400 mL) was added and the resulting two-phase system was vigorously stirred while lowering the pH of the aqueous layer to two.

After transferring to a separatory funnel and separating the layers, the aqueous layer was washed with additional ethyl acetate (2×100 mL). The combined product-rich, organic layers were washed with half-saturated brine (1×240 mL) and brine (1×200 mL) and dried over sodium sulfate. The organic solution was filtered and concentrated in vacuo at ≦30° C. The resulting solid phthalamic acid derivative was dried under high vacuum to 29.17 g.

The phthalamic acid derivative was dissolved in tetrahydrofuran (150 mL) and evaporated to remove traces of ethyl acetate. The material was dissolved in tetrahydrofuran (243 mL including the amount left after the evaporation) and added to a 500-mL flask equipped with mechanical stirrer and argon inlet. Anhydrous oxalic acid (13.437 g, 149 mmol) was added followed by water (68 mL). The resulting hazy solution was stirred at a gentle reflux under argon for 6.5 hours. Heating was discontinued and the mixture stirred overnight.

The resulting crystal slurry was stirred while cooling at 0° C. for 4 hours. The product was filtered and washed with tetrahydrofuran (2×140 mL), ethyl acetate (3×140 mL), and hexane (3×140 mL). The title compound was dried under high vacuum, initially at room temperature to a constant weight of 18.899 g, and then at 50° C. overnight to 18.880 g.

Melting point: 184°–187° C.

21-B.  [1S-[1α,2α(Z),3α,4α]]-7-[(3-Aminomethyl)-7-oxabicyclo[2.2.1]hept-2-yl]-5-heptanoic acid

Method I

A suspension of [1S-[1α,2α(Z),3α,4α]-7-[(3-aminomethyl) -7-oxabicyclo[2.2.1]hept-2-yl]-5-heptenoic acid, oxalate (1:1) salt (6.72 g corrected weight, 19.568 mmol; containing 2.25% trans olefin by HPLC) in methanol (70 mL) was stirred under argon and treated over 5 minutes with triethylamine (6.73 mL, 41.1 mmol). An additional 6 mL of methanol was added and the heavy slurry was stirred at room temperature overnight. The slurry was filtered and the crude product was washed with methanol, ether, and hexane and dried in vacuo to 3.55 g (72%) of the title compound containing 0.64% trans olefin by HPLC.

A portion of the product (3.0 g) was slurried in methanol-water (18 mL–4.5 mL) and stirred overnight. The slurry was filtered and washed with 15% aqueous methanol, methanol, ether and hexane. After drying in vacuo the product weighed 2.224 g and contained ≦0.05% olefin by HPLC.

Melting Point: 223°–235° C. with decomposition.

The mother liquors from a large scale run (606 g input of oxalate salt) were combined and concentrated in vacuo using toluene to remove water. The residue was slurried in methanol (3 L), stirred overnight and filtered to afford 294 g of [1S-[1α,2α(Z),3α,4α]]-7-[(3-aminomethyl)-7-oxabicyclo-[2.2.1]hept-2-yl-5-heptenoic acid, hemixalate salt. This material was slurried in methanol (2200 mL), treated with triethylamine (100.32 g) and stirred at room temperature overnight. The slurry was filtered and washed with methanol and ether to afford 217 g of the title compound.

Method II

A 3-necked flask equipped with overhead stirrer and reflux condenser was charged with [1S-[1α,2α(Z),3α,4α]]-7-[(3-aminomethyl)-7-oxabicyclo[2.2.1]hept-2-yl]-5-heptenoic acid, 1:1 oxalate salt (10 g, 28.29 mmol after correction for residual water; 3.7% trans double bond isomer by HPLC), methanol (60 mL), and water (8 mL). The mixture was cooled in an ice bath and treated with triethylamine (8.3 mL, 59.41 mmol). The cooling bath was removed and the slurry was stirred at ambient temperature for 20 minutes and then heated to reflux. Water was added slowly via the condenser until a clear solution was obtained (12 to 13 mL required). An additional 1 mL of water was then added, and the mixture was cooled while stirring and seeded at a bath temperature of 40° C. Stirring was continued at ambient temperature overnight, and then at 0° C. for several hours.

The product was filtered and washed with 5% aqueous methanol (3×10 mL), methanol (3×20 mL), ether (3×25 mL), and hexane (3×25 mL). The yield of the title compound was 4.84 g (68%). HPLC indicated the presence of 0.5% trans double bond isomer.

Melting point: 234°–235° C. with decomposition.

A slurry of 1 g of this product in 6 mL of methanol was treated with 2.5 mL of water. The resulting slurry was stirred at room temperature overnight and filtered. The product was washed with 70% methanol-water, methanol, ether, and hexane. The recovery of the title compound was 656 mg. HPLC analysis indicated ≦0.05% trans double bond isomer.

21-C.  [1S-[1α,2α(Z),3α,4α]]-7-[3-[[[[(1-Oxoheptyl)amino]acetyl]amino]methyl]-7-oxabicyclo[2.2.1]hept-2-yl]-5-heptenoic acid

Method I

A suspension of [(1-oxoheptyl)amino]acetic acid (2.673 g, 14.273 mmol) in dichloromethane (80 mL) was stirred under argon at 0° C. and treated with solid 1,1-carbonyldiimidazole (CDI; 22.5 g, 13.873 mmol) over 3 minutes. The resulting suspension was stirred briefly at 0° C. and then at room temperature for 2.5 hours. The resulting solution was cooled to 0° C. and treated with solid 1S-[1α,2α(Z),3α,4α]]-7-[3-aminomethyl)-7-oxabicyclo[2.2.1]hept-2-yl]-5-heptenoic acid, oxalate (1:1) salt (4.7 g, 13.339 mmol), followed by N,N-diisopropylethylamine (7.09 mL, 40.685 mmol). The reaction was stirred vigorously for 4 hours and treated with 1 N HCl (40 mL). Additional HCl was then added to lower the pH of the aqueous layer to 2.5. The biphasic mixture was transferred to a separatory funnel, the layers were separated and the aqueous layer was extracted with dichloromethane (3×10 mL). The three organic extracts were added to the original dichloromethane layer and the resulting organic solution was washed with 1 N HCl (3×50 mL), water (3×40 mL), and brine (1×50 mL).

The organic solution was concentrated in vacuo to a small volume, and ethyl acetate was added and evaporated. The resulting solid was recrystallized from ethyl acetate. The product was filtered, washed with ethyl acetate and hexane and dried in vacuo. The yield of the title compound was 4.895 g (86%).

Melting point: 117° to 119° C.

Method II

A suspension of [(1-oxoheptyl)amino]acetic acid (102.75 g, 0.55 mol) in dichloromethane (2600 mL) was chilled to 0° C. under a gentle sweep of argon and treated with carbonyldiimidazole (CDI) (85.16 g, 0.525 mol) in one portion. The reaction mixture was stirred at 0° C. for about five minutes then warmed to 25° C. over fifteen minutes. The reaction was then stirred at 25° C. (internal temperature maintained with a warm water bath) for three hours. The resultant solution was chilled at 0° C., treated with diisopropylethylamine (85.67 g, 0.66 mol), stirred for about five minutes, then treated with powdered [1S-[1α,2α(Z),3α,4α]]-7-[(3-aminomethyl)-7-oxabicyclo[2.2.1]hept-2-yl]-5-heptenoic acid, (129.7 g, 0.51 mol with residual water correction). The reaction slurry was stirred at 0 to 2° C. for five hours.

The slurry was treated with 1800 mL of 1 N HCl in one portion (exotherm to 22° C.), stirred for about five minutes, then the layers were separated. The acidic aqueous layer (pH 2.1) was extracted with dichloromethane (3×400 mL). The combined organic layers were washed with 1 N HCl (3×2 liter) and water (3×2 liter). Each aqueous layer was extracted with dichloromethane (200 mL) and added to the main extract before each subsequent wash. The organic layer was dried over magnesium sulfate, filtered, and concentrated in vacuo to a dry solid (220 g).

The residue was combined with ethyl acetate (2550 mL) and heated until dissolution, then left standing at room temperature overnight. The resultant solid was filtered and the solid washed sequentially on the frit with ethyl acetate (3×600 mL) and hexane (3×600 mL) to yield 170 g of the title compound.

Melting point: 116°-118° C. [α]$_D$=7.1° (c=1,methanol).

What is claimed is:

1. A process for preparing a cis acid of the formula

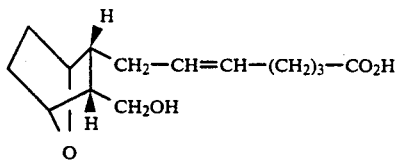

which comprises:
(a) reacting a halide of the formula

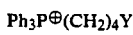

(wherein Ph is phenyl, halo is chloro, bromo or iodo, and Y is CO$_2$⊖K⊕, CO$_2$H or —C≡N) with a potassium butoxide, amylate, hydride or disilazide to form an ylide of the formula

and
(b) reacting the ylide with a pyranol of the formula

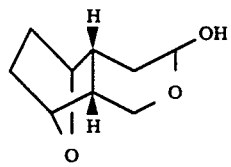

in tetrahydrofuran.

2. The process of claim 1, wherein halo is bromo.
3. The process of claim 1, wherein the ylide is prepared in situ.
4. The process of claim 1, wherein Y is —CO$_2$H.
5. The process of claim 1, wherein the halide and the alkali metal compound are reacted in tetrahydrofuran.
6. The process of claim 1, further comprising:
(a) neutralizing the acid to form an amine salt of the formula

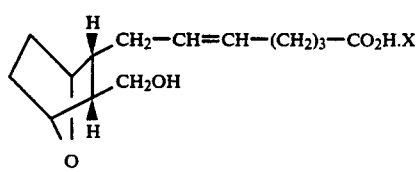

wherein X is adamantanamine; and
(b) recovering the amine salt.
7. The process of claim 6, further comprising reacting the amine salt with an alcohol of the formula

ROH (wherein R is alkyl, cycloalkyl, alkaryl, or aralkyl) in the presence of an acid to form an ester of the formula

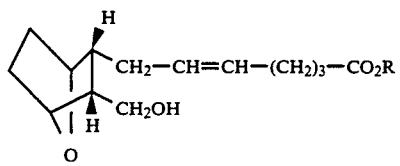

wherein
"alkyl" and "alk-" refer to straight or branched chain hydrocarbon groups of 1 to 12 carbon atoms;
"aryl" and "alk-" refer to monocyclic or bicyclic aromatic groups having from six to ten carbon atoms in the ring portion, which may be substituted with nitro, halo, methyl, or alkoxy; and
"cycloalkyl" refers to a cyclic alkyl group.
8. The process of claim 7, wherein the alcohol is methanol.
9. The process of claim 7, wherein the acid is hydrochloric acid.
10. The process of claim 7, wherein the ylide is prepared by reacting a halide of the formula

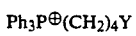

(wherein halo is chloro, bromo or iodo) with an alkali metal butoxide, amylate, hydride, or disilazide.
11. The process of claim 7, wherein Y is —CO$_2$H.
12. The process of claim 10, wherein halo is bromo.

13. The process of claim 10, wherein the ylide is prepared in situ.

14. The process of claim 10, wherein the halide and the alkali metal compound are reacted in tetrahydrofuran.

15. The process of claim 7, further comprising:
(a) reacting the ester with an activating reagent and aminating reagent, followed by a base to form a diacid of the formula

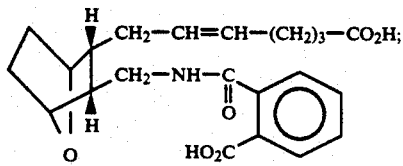

(b) hydrolyzing the diacid with water and an aqueous acid in the presence of an organic co-solvent with heating at reflux to form an amino acid of the formula

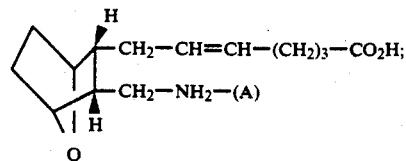

wherein is a conjugate acid; and (c) acylating the amino acid with [(1-oxoheptyl)amino]acetic acid in the presence of 1,1-carbonyldiimidazole and a tertiary amine base selected from N,N-diisopropylethylamine, tributylamine, triethylamine, and 1,8-diazabicyclo[5.4.0]undec-7-ene to form [1S-[1α,2α(Z),3α,4α]]-7-[3[[[[(1-oxoheptyl)amino]acetyl]amino]methyl-7-oxabicyclo[2.2.1-]hept-2-yl]-5-heptenoic acid.

16. The process of claim 15, further comprising neutralizing the amino acid prior to the acylation.

17. The process of claim 1, wherein the step (b) reaction is quenched with acetic acid.

18. The process of claim 1, wherein the reaction in step (b) is conducted in an inert atmosphere.

* * * * *